(12) United States Patent
Komatsubara et al.

(10) Patent No.: US 9,462,788 B2
(45) Date of Patent: Oct. 11, 2016

(54) ABSORBENT ARTICLE FOR PET

(75) Inventors: Daisuke Komatsubara, Kagawa (JP); Takeshi Ikegami, Kagawa (JP)

(73) Assignee: Unicharm Corporation, Ehime (JP)

( * ) Notice: Subject to any disclaimer, the term of this patent is extended or adjusted under 35 U.S.C. 154(b) by 103 days.

(21) Appl. No.: 14/007,493

(22) PCT Filed: Mar. 13, 2012

(86) PCT No.: PCT/JP2012/056469
§ 371 (c)(1),
(2), (4) Date: Nov. 27, 2013

(87) PCT Pub. No.: WO2012/132887
PCT Pub. Date: Oct. 4, 2012

(65) Prior Publication Data
US 2014/0083372 A1 Mar. 27, 2014

(30) Foreign Application Priority Data
Mar. 30, 2011 (JP) .................................. 2011-075846

(51) Int. Cl.
*A01K 13/00* (2006.01)
*A01K 23/00* (2006.01)
*A61F 13/15* (2006.01)

(52) U.S. Cl.
CPC ...... *A01K 23/00* (2013.01); *A61F 2013/15186* (2013.01)

(58) Field of Classification Search
CPC ..................... A01K 23/00; A61F 2013/15186
USPC .......................... 119/850, 867, 868, 869, 171
See application file for complete search history.

(56) References Cited

U.S. PATENT DOCUMENTS 3,738,330 A * 6/1973 Alofsin ......................... 119/838
3,927,674 A * 12/1975 Schaar ..................... 604/385.13
4,209,016 A * 6/1980 Schaar ........................... 604/390

(Continued)

FOREIGN PATENT DOCUMENTS

JP 2004-159592 A 6/2004
JP 2005-229915 A 9/2005

(Continued)

OTHER PUBLICATIONS

International Search Report from corresponding PCT application No. PcT/JP2012/056469 dated May 15, 2012 (4 pgs).

(Continued)

*Primary Examiner* — Kristen C Hayes
*Assistant Examiner* — Ebony Evans
(74) *Attorney, Agent, or Firm* — Brinks Gilson & Lione

(57) ABSTRACT

An absorbent article for pet includes: a liquid permeable top surface layer; a liquid impermeable back surface layer; and an absorbent core disposed between the top and back surface layer, and configured in a rectangular shape with a first end portion and a second end portion facing each other and a pair of side portions facing each other, and in a state in which the absorbent article is wrapped around a waist of a pet, the first end portion is positioned on a pet's body side and the second end portion is detachably attached to an outer face of the first end portion, in which the absorbent article for pet further includes elastic members disposed along the longitudinal direction of the absorbent article in an extended state; and a high stiffness portion that is higher in stiffness than the second end portion is formed in the first end portion.

8 Claims, 15 Drawing Sheets

(56) References Cited

U.S. PATENT DOCUMENTS

| | | | | |
|---|---|---|---|---|
| 4,996,949 | A | * | 3/1991 | Wunderman et al. ........ 604/390 |
| 5,137,508 | A | * | 8/1992 | Engman ........................ 602/79 |
| D383,259 | S | * | 9/1997 | Post ............................. D30/145 |
| 6,371,950 | B1 | * | 4/2002 | Roslansky ............ A61F 13/471 604/385.01 |
| D624,249 | S | * | 9/2010 | Ramos et al. ............... D30/145 |
| D693,524 | S | * | 11/2013 | Jangula ....................... D30/145 |
| 2007/0129702 | A1 | * | 6/2007 | Gribben ....................... 604/392 |
| 2010/0094235 | A1 | | 4/2010 | Solomon et al. |
| 2010/0319633 | A1 | * | 12/2010 | Moncheski .................. 119/869 |
| 2011/0209675 | A1 | * | 9/2011 | Esperon ....................... 119/868 |
| 2014/0165926 | A1 | * | 6/2014 | Marks .......................... 119/838 |

FOREIGN PATENT DOCUMENTS

| | | |
|---|---|---|
| JP | 2007-20533 A | 2/2007 |
| JP | 3141580 | 4/2008 |

OTHER PUBLICATIONS

European extended Search Report from corresponding European application No. 12764529.9 dated Jul. 29, 2014 (6 pgs).

* cited by examiner

ABSORBENT ARTICLE FOR PET

RELATED APPLICATION

This application is a 35 U.S.C. §371 national phase filing of International Patent Application No. PCT/JP2012/056469 filed Mar. 13, 2012, to which priority is claimed under 35 U.S.C. §120 and through which priority is claimed under 35 U.S.C. §119 to Japanese Patent Application No. 2011-075846, filed Mar. 30, 2011.

TECHNICAL FIELD

The present invention relates to an absorbent article for pet, which is used in a state of being wrapped around waist of pet such as dog and cat.

BACKGROUND ART

Heretofore, a disposable diaper for pet used for pet such as dog and cat has been proposed. Such a disposable diaper for pet catches feces and urine of pet by covering the anus and the urethral opening positioned between bases of hind legs when being worn.

Some of pets (for example miniature dachshund) have the urethral opening more in front than a position between bases of hind legs. In addition, male dogs have the urethral opening more in front than female dogs. If the disposable diaper for pet is used for pets having the urethral opening more in front than a position between bases of hind legs, the urethral opening may not be covered by the diaper and urine may leak.

Given this, an absorbent article for pet that is configured in a rectangular shape and worn in a state of being wrapped around the pet's waist is proposed (for example see Patent Document 1).

Such an absorbent article for pet configured in a belt-like shape can cover the urethral opening, regardless of position thereof.

Patent Document 1: Japanese Unexamined Patent Application Publication No. 2007-20533

DISCLOSURE OF THE INVENTION

Problems to be Solved by the Invention

The absorbent article for pet used in a state of being wrapped around the pet's waist, as proposed in Patent Document 1, is put on to the pet in the following steps, for example.

First, a first end portion in the longitudinal direction of the absorbent article for pet is placed on the back of the pet and the vicinity of the first end portion is held by one hand of a user. Thereafter, in a state in which the first end portion is held by one hand, a second end portion of the absorbent article for pet is held by the other hand and wrapped around the pet's body to cover the abdomen of the pet. And then, the second end portion of the absorbent article for pet is pulled to bring a side portion of the absorbent article for pet along a longitudinal direction into close contact with the waist of the pet, and, in this state, an inner face of the second end portion of the absorbent article for pet is engaged with an outer face of the first end portion. The absorbent article for pet can thus be maintained in a state of being appropriately wrapped around the pet's waist.

In such an absorbent article for pet as described above, when the second end portion of the absorbent article for pet is pulled in order to wrap around the pet's waist, a force of pulling the second end portion may lift the first end portion of the absorbent article for pet being held by one hand. If the first end portion of the absorbent article for pet is lifted during wearing, it becomes difficult to engage the outer face of the first end portion with the inner face of the second end portion of the absorbent article for pet. As a result, it becomes difficult to put the absorbent article for pet around the pet's waist.

Especially in an absorbent article for pet in which an elastic member such as rubber is disposed in a side portion along a longitudinal direction, the absorbent article for pet is in a form of being contracted in the longitudinal direction in a natural state. Given this, in order to bring the absorbent article for pet around the pet's waist in a state of being extended, a user must strongly pull the second end portion. As described above, in the absorbent article for pet in which the elastic member such as rubber is disposed, the second end portion is strongly pulled and the first end portion of the absorbent article for pet is even more likely to lift. This makes it more difficult to put the absorbent article for pet around the pet's waist.

In view of the above, the present invention is aimed at providing an absorbent article for pet that facilitate putting at a proper position upon wrapping the absorbent article for pet around the pet's waist.

Means for Solving the Problems

The present invention relates to an absorbent article for pet including: a top surface layer that is liquid permeable; a back surface layer that is liquid impermeable; and an absorbent core disposed between the top surface layer and the back surface layer, the absorbent article for pet being configured in a rectangular shape with a first end portion and a second end portion facing each other and a pair of side portions facing each other orthogonal to the first end portion and the second end portion, and in a state in which the absorbent article for pet is wrapped around a waist of a pet, the first end portion is positioned on a pet's body side and the second end portion is detachably attached to an outer face of the first end portion, in which: the absorbent article for pet further includes an elastic member that is disposed along a longitudinal direction of the absorbent article for pet in a state of being extended; and a high stiffness portion that is higher in stiffness than the second end portion is formed in the first end portion.

In addition, it is preferable that the absorbent article for pet further includes: a pair of side sheets, which is respectively disposed on the top surface layer side of the pair of side portions, an outer edge of which is joined with the top surface layer or the back surface layer and at least a part of an inner edge of which is a free end; and a pair of pocket portions that is formed between an inner face of the pair of side sheets and an outer face of the top surface layer, wherein the elastic member is disposed in the vicinity of the inner edge of each of the pair of side sheets.

In addition, it is preferable that the elastic member is disposed respectively on the pair of side portions.

In addition, it is preferable that a belt-like tape member with a plurality of hook portions is attached to the outer face of the first end portion; and an inner face of the second end portion is constituted of a nonwoven fabric constituting at least one of the top surface layer and the side sheet.

In addition, it is preferable that the tape member is attached at a position away from an end edge of the first end portion by a predetermined distance, so as to extend in a width direction of the absorbent article for pet.

Effects of the Invention

The absorbent article for pet according to the present invention can be put at a proper position upon wrapping the absorbent article for pet around the pet's waist.

DESCRIPTION OF REFERENCE NUMERALS

Figure 1:
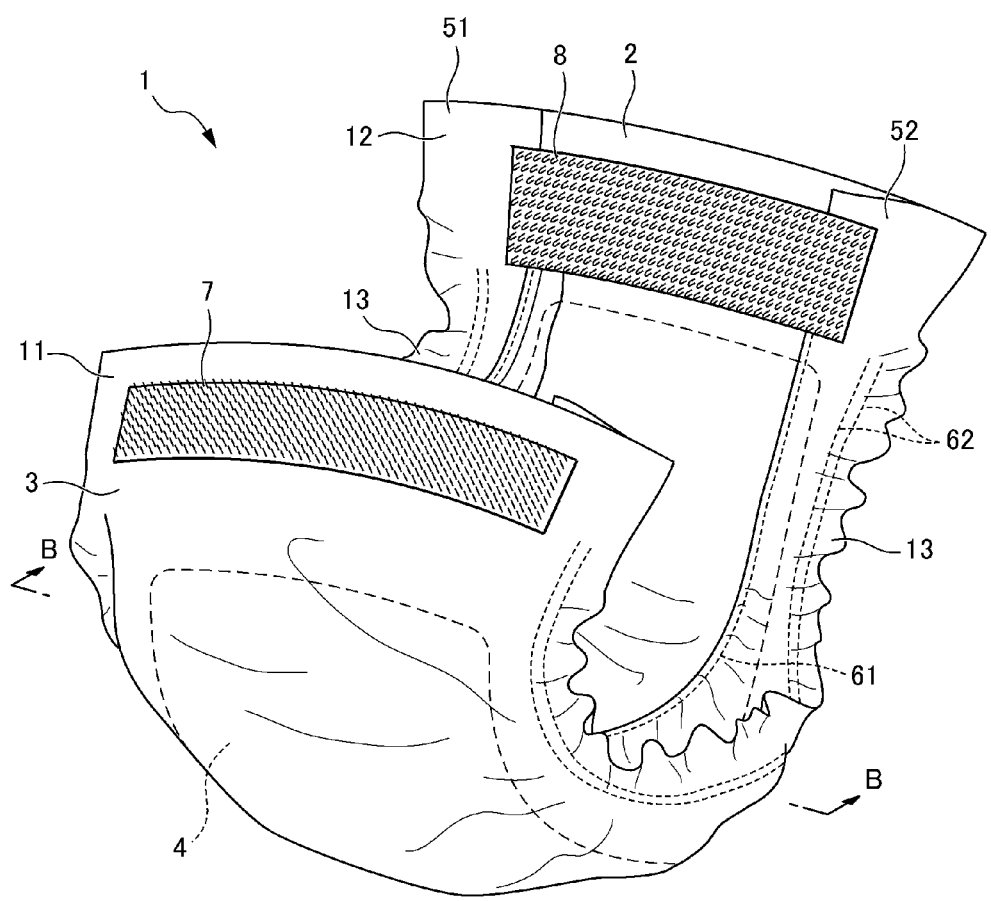
FIG. 1 is a perspective view showing an absorbent article for pet according to a first embodiment of the present invention.

1 Absorbent article for pet
2 Top sheet (Top layer)
3 Back surface layer
4 Absorbent core
7 Hook tape (Tape member)
11 First end portion
12 Second end portion
14 Pocket portion
15 Pocket portion
51 Front side sheet (Side sheet)
52 Rear side sheet (Side sheet)
61 First elastic member (Elastic member)
62 Second elastic member (Elastic member)

PREFERRED MODE FOR CARRYING OUT THE INVENTION

Embodiments of the absorbent article for pet according to the present invention will be described hereinafter with reference to the drawings.

First, the absorbent article for pet according to the first embodiment will be described hereinafter with reference to FIGS. 1 to 5.

Figure 2:
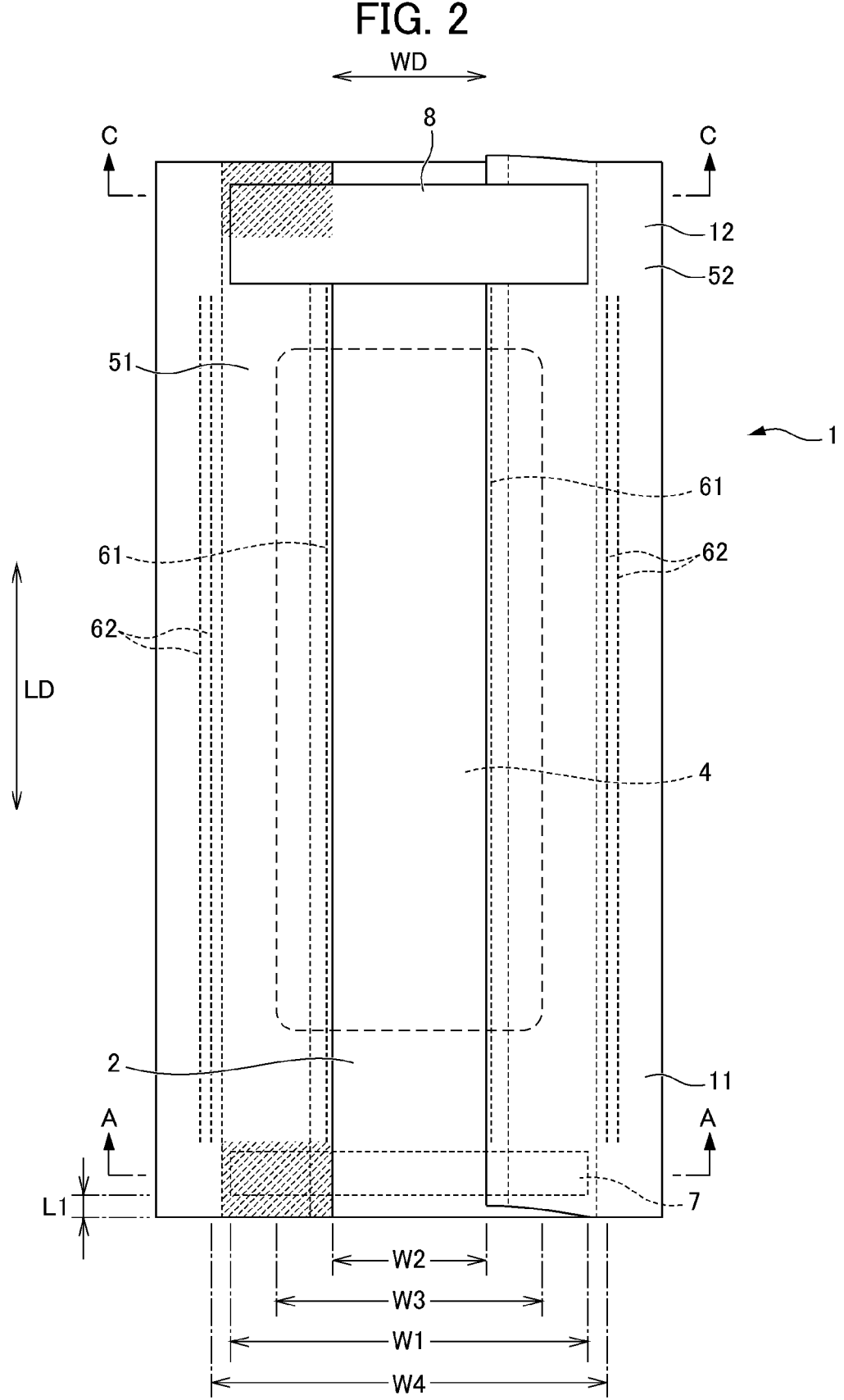
FIG. 2 is a plan view of the absorbent article for pet according to the first embodiment.

As shown in FIGS. 1 and 2, an absorbent article for pet 1 according to the first embodiment is configured in a rectangular shape with a first end portion 11 and a second end portion 12, as a pair of end portions, facing each other and a pair of side portions facing each other orthogonal to the first end portion 11 and the second end portion 12, the absorbent article for pet 1 being worn in a state of being wrapped around the waist of a pet. The absorbent article for pet 1 is especially preferably used for a pet having the urethral opening located further toward the front than a position between bases of hind legs (such as miniature dachshund).

The absorbent article for pet 1 includes, as shown in FIGS. 1 to 5: a top sheet 2 constituting the liquid permeable top surface layer; a back surface sheet 31 and a waterproof sheet 32 constituting the liquid impermeable back surface layer 3; an absorbent core 4; a pair of side sheets 51, 52; a first elastic member 61 and a second elastic member 62 as an elastic member; a hook tape 7 as the tape member; and a loop member 8 that can engage with the hook tape 7.

The top sheet 2 is configured in a rectangular shape. The top sheet 2 mainly configures a surface of a side in contact with the pet's body, which is an object to wear the absorbent article for pet. As the top sheet 2, a perforated or non-perforated nonwoven fabric and a porous plastic sheet can be used.

Figure 3:
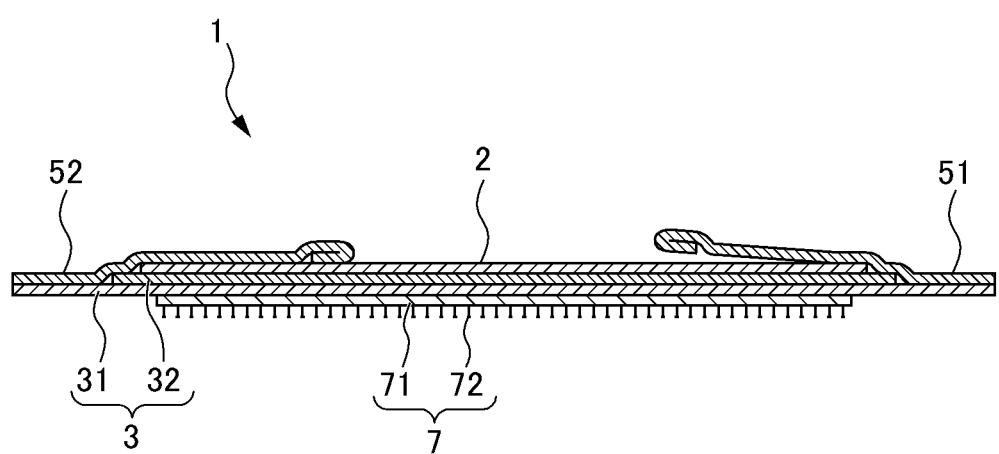
FIG. 3 is a cross-sectional view taken along the line A-A of FIG. 2.
Figure 4:
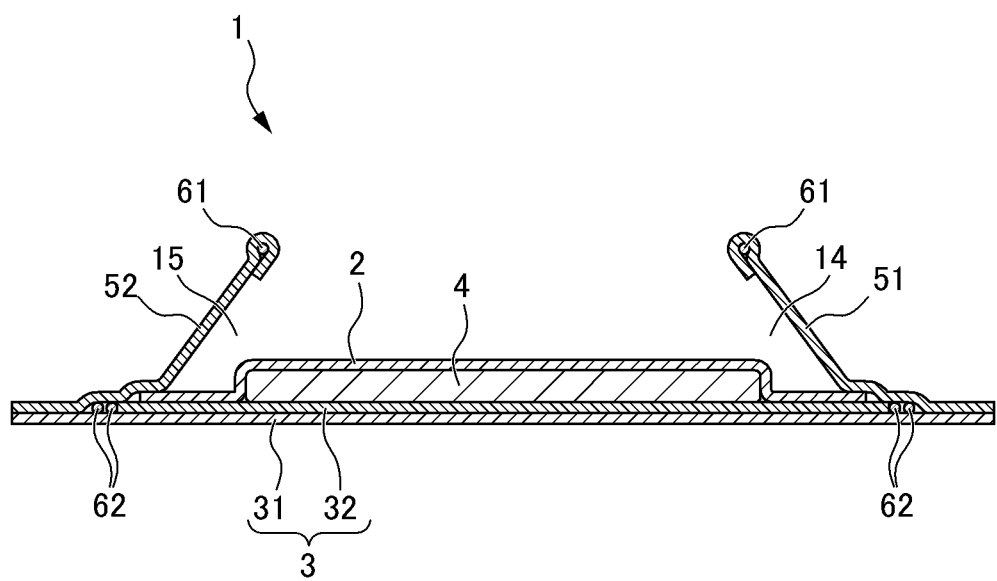
FIG. 4 is a cross-sectional view taken along the line B-B of FIG. 1.
Figure 5:
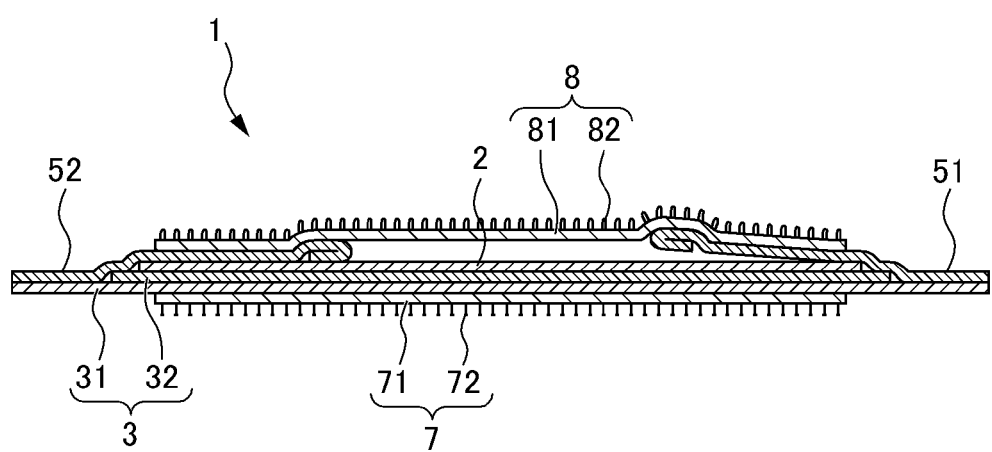
FIG. 5 is a cross-sectional view taken along the line C-C of FIG. 2.

The back surface sheet 31 is configured in a rectangular shape that is wider than, and has substantially the same length as, the top sheet 2, as shown in FIGS. 3 to 5. The back surface sheet 31 constitutes a surface of the absorbent article for pet 1, on a side not in contact with the pet's body.

The waterproof sheet 32 is configured to be smaller in width than the back surface sheet 31 and greater in width than the top sheet 2 and disposed on a top sheet 2 side of the back surface sheet 31.

As the back surface sheet 31 and the waterproof sheet 32, a hydrophobic nonwoven fabric, a liquid impermeable plastic film, a laminated sheet made of the nonwoven fabric and the liquid impermeable plastic film, an SMS nonwoven fabric made by sandwiching a high-water resistance melt-blown nonwoven fabric with a high-strength spun-bond nonwoven fabric, and the like can be used.

The absorbent core 4 is disposed between the top sheet 2 and the back surface layer 3 that are layered, as shown in FIG. 4. The absorbent core 4 is configured in a rectangular shape smaller in width and length than the top sheet 2 and the back surface sheet 31. As shown in FIG. 2, the absorbent core 4 is disposed in a substantially central portion in the width direction of the top sheet 2 and the back surface sheet 31, from a first end side to a second end side in the longitudinal direction. As the absorbent core 4, fluff pulp and high absorbance polymer wrapped with a core wrapping material such as tissue can be used.

As the fluff pulp used in the absorbent core 4, chemical pulp, cellulose fiber, and artificial cellulose fiber such as rayon, acetate, and the like can be exemplified. As the high absorbance polymer, granulous or fibrous polymer of starch, acrylic acid, and amino acid can be exemplified.

The pair of side sheets 51, 52 are configured in an elongated rectangular shape as shown in FIG. 2 and disposed on respective side portions along the longitudinal direction of the top sheet 2 on a body side thereof. The pair of side sheets 51, 52 is configured to have substantially the same length as the top sheet 2 and the back surface sheet 31. As shown in FIGS. 3 to 5, outer edges of the pair of side sheets 51, 52 correspond to side edges of the back surface sheet 31. The outer edges of the pair of side sheets 51, 52 are joined with the side edges of the back surface sheet 31.

A part of the inner edges of the pair of side sheets 51, 52 is a free-end, as shown in FIGS. 1 and 4. More specifically, the pair of side sheets 51, 52 includes a front side sheet 51 that is placed on a front side of the pet's body and a rear side sheet 52 that is placed on a back side of the pet's body upon putting the absorbent article for pet 1 on the pet.

The inner edge of the front side sheet 51 is joined to the top sheet 2 in the first end portion 11 and the second end portion 12, as shown in FIGS. 3 and 5. In addition, the inner edge of the front side sheet 51 is a free end, except for the first end portion 11 and the second end portion 12, as shown in FIG. 4.

As shown in FIGS. 3 to 5, the inner edge of the rear side sheet 52 is a free end in the entire length in the longitudinal direction LD of the absorbent article for pet 1.

As the side sheets 51, 52, a water repellent or hydrophobic sheet is preferably used. More specifically, various nonwoven fabrics such as spun lace nonwoven fabric, spunbond nonwoven fabric, thermal bond nonwoven fabric, meltblown nonwoven fabric, needle-punched nonwoven fabric, air-through nonwoven fabric and the like can be used. As the fiber composing the nonwoven fabric, synthetic fiber of olefin, polyester, polyamide and the like such as polyethylene and polypropylene; regenerated fiber such as rayon and cupra; and natural fiber such as cotton can be used.

The first elastic member 61 is disposed in the vicinity of the respective inner edge of the front side sheet 51 and the rear side sheet 52, as shown in FIGS. 1 and 2. More specifically, the first elastic member 61 is sandwiched by the side sheet that is folded back from the inner edge side and fixed to the side sheet by a hotmelt adhesive in an extended state as shown in FIG. 4. The first elastic member 61 is, in the extended state, greater in length than the absorbent core 4 in the longitudinal direction and is disposed on the front side sheet 51 and the rear side sheet 52 as shown in FIG. 2.

The second elastic member 62 is disposed on each of the pair of side portions along the longitudinal direction LD of the absorbent article for pet 1, as shown in FIGS. 1 and 2. More specifically, the second elastic member 62 is disposed between the front side sheet 51 and back surface sheet 31, and between the rear side sheet 52 and the back surface sheet 31, as shown in FIG. 4. In addition, the second elastic member 62 is fixed to the side sheets 51, 52 and the back surface sheet 31 by a hotmelt adhesive.

The second elastic member 62 is, in the extended state, greater in length than the absorbent core 4 in the longitudinal direction and is disposed on each of the pair of side portions along the longitudinal direction LD of the absorbent article for pet 1.

As the first elastic member 61 and the second elastic member 62, any material that is elongated and stretchable can be used, for example: natural rubber such as filiform rubber and flat rubber; thermoplastic elastomer such as urethane, ethylene-vinyl acetate copolymer (EVA), and PE. More specifically, as the thermoplastic elastomer, polybutadiene, polyisoprene, styrene-butadiene copolymer, styrene-isoprene copolymer, polyurethane, ethylene-vinyl acetate copolymer, ethylene-a-olefin copolymer and the like that are processed to be filiform or formed in a film and then slit into thin strips can be exemplified.

The hook tape 7 is disposed on an outer face of the first end portion 11 of the absorbent article for pet 1, as shown in FIGS. 1 and 2. The hook tape 7 is configured in a belt like shape and disposed such that the longitudinal direction thereof is along the width direction WD of the absorbent article for pet 1. In addition, it is preferable that the hook tape 7 is attached at a position away from the side edge of the first end portion 11 by a predetermined distance L1.

As shown in FIG. 3, the hook tape 7 includes a belt-shaped base portion 71 and a plurality of hook portions 72 provided on one face of the base portion 71. The hook tape 7 is attached to the back surface sheet 31 such that the face on which the plurality of hook portions 72 is formed is directed outward.

In the hook tape 7, the base portion 71 and the plurality of hook portions 72 are integrally formed with a synthetic resin material such as polypropylene. It is preferable that the hook tape 7 has a predetermined bending stiffness, in order to increase the bending stiffness of the first end portion 11.

In order to secure the bending stiffness of the first end portion 11 in the width direction WD, a length W1 of the hook tape 7 in the width direction WD of the absorbent article for pet 1 is preferably greater than a length W2 between the first elastic member 61 attached to the front side sheet 51 and the first elastic member 61 attached to the rear side sheet 52, and more preferable greater than the length W3 of the absorbent core 4 in the width direction. In addition, in order to maintain a desirable fit of the absorbent article for pet 1, a length W1 of the hook tape 7 in the width direction WD of the absorbent article for pet 1 is preferably smaller than a length W4 between the second elastic members 62 respectively disposed in a pair of side portions along the longitudinal direction LD of the absorbent article for pet 1.

A distance L1 from the end edge of the first end portion 11 to the side edge of the hook tape 7 is preferably 5 mm to 50 mm, more preferably 10 mm to 30 mm. If the distance L1 from the end edge of the first end portion 11 to the side edge of the hook tape 7 is smaller than 5 mm, the pet's coat may be caught by the hook tape 7 when the absorbent article for pet 1 is put on the pet's body. On the other hand, if the distance L1 from the end edge of the first end portion 11 to the side edge of the hook tape 7 is greater than 50 mm, it may not be possible to secure sufficient lengths of the pocket portions 14, 15 (described later).

The loop member 8 is disposed on an inner face of the second end portion 12 of the absorbent article for pet 1, as shown in FIGS. 1 and 2. The loop member 8 is configured in a belt-like shape and disposed such that the longitudinal direction thereof is along the width direction WD of the absorbent article for pet 1. As shown in FIG. 5, the loop member 8 has a belt-like base portion 81 and a plurality of loop portions 82 provided on one face of the base portion 81. The loop member 8 is attached to the top sheet 2 and the side sheets 51, 52 such that a face on which the plurality of loop portions 82 is formed is directed to the inner side of the absorbent article for pet 1.

In the loop member 8, the base portion 81 and the plurality of loop portions 82 are integrally formed with a synthetic resin material such as polyester. The bending stiffness of the loop member 8 is configured to be smaller than the bending stiffness of the hook tape 7.

In the above described absorbent article for pet 1, the stiffness in the width direction WD of a region in which the hook tape 7 is disposed in the first end portion 11, represented by bending resistance measured by the bending resistance measuring method A (45° cantilever method) defined by L1084 (testing method for flocked fabrics), is preferably 100 mm to 200 mm.

In addition, the stiffness (bending resistance) in the width direction WD of a region in which the hook tape 7 is disposed in the first end portion 11 is configured to be greater than the stiffness (bending resistance) in the width direction WD of a region in which the loop member 8 is disposed in the second end portion 11.

In the above-described absorbent article for pet 1, the first elastic member 61 in the extended state is fixed to the front side sheet 51 and the rear side sheet 52 along the longitudinal direction LD of the absorbent article for pet 1. In addition, the second elastic member 62 in the extended state is fixed between the side sheets 51, 52 and the back surface sheet 31, along the longitudinal direction LD of the absorbent article for pet 1.

Given this, the absorbent article for pet 1 in a natural state (without external force applied) has a solid shape as shown in FIG. 1, with the first elastic member 61 and the second elastic member 62 being contracted to thereby bring the first end portion 11 and the second end portion 12 close to each other, with the top sheet 2 side composing an inner face. A pair of waist gather portions 13 that are stretchable in the longitudinal direction LD are thus formed on a pair of side portions in the longitudinal direction LD of the absorbent article for pet 1 (see FIG. 1). In addition, free end sides of the front side sheet 51 and the rear side sheet 52 lift, to thereby form pocket portions 14, 15 between the inner face of the front side sheet 51 and the outer face of the top sheet 2, as well as between the inner face of the rear side sheet 52 and the outer face of the top sheet 2 (see FIG. 4).

The hook tape 7 is disposed in the first end portion 11 of the absorbent article for pet 1, and the loop member 8 is disposed in the second end portion 12. The bending stiffness of the hook tape 7 is greater than the bending stiffness of the loop member 8. Therefore, in a part of the first end portion 11 of the absorbent article for pet 1 in which the hook tape 7 is disposed, a high stiffness portion is formed that is greater in bending stiffness than a part of the second end portion 12 in which the loop member 8 is disposed.

Figure 6:
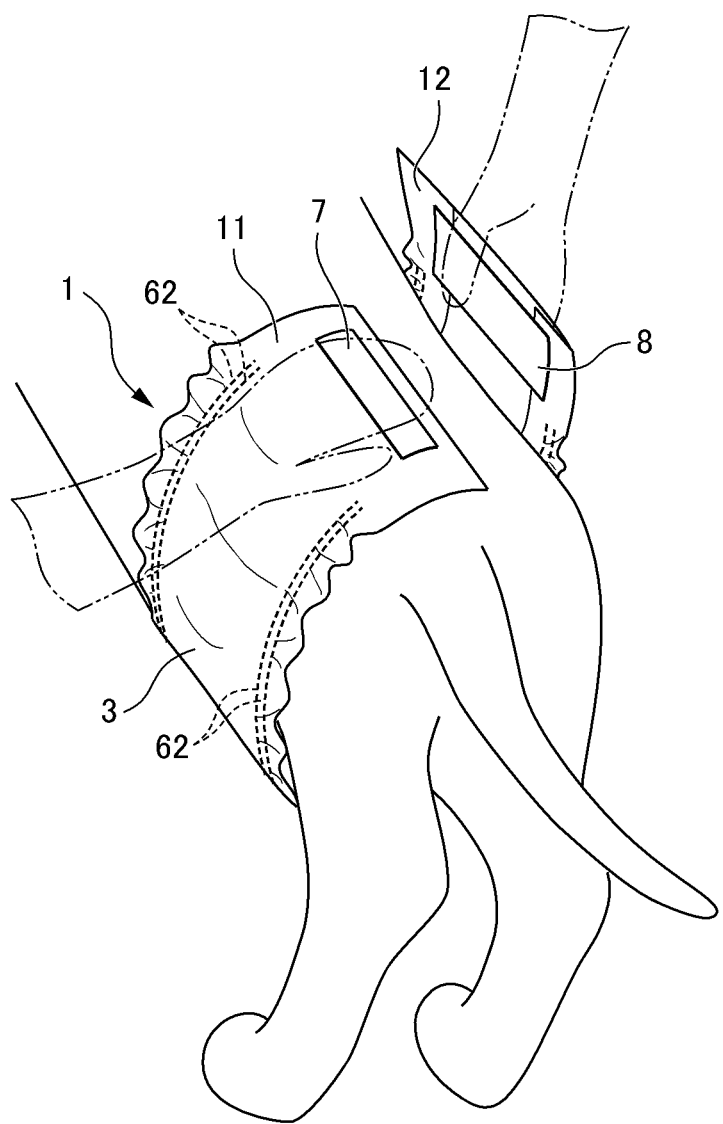
FIG. 6 is a diagram illustrating a process of putting the absorbent article for pet of the first embodiment on a pet, in which the first end portion is placed on the pet's back.
Figure 7:
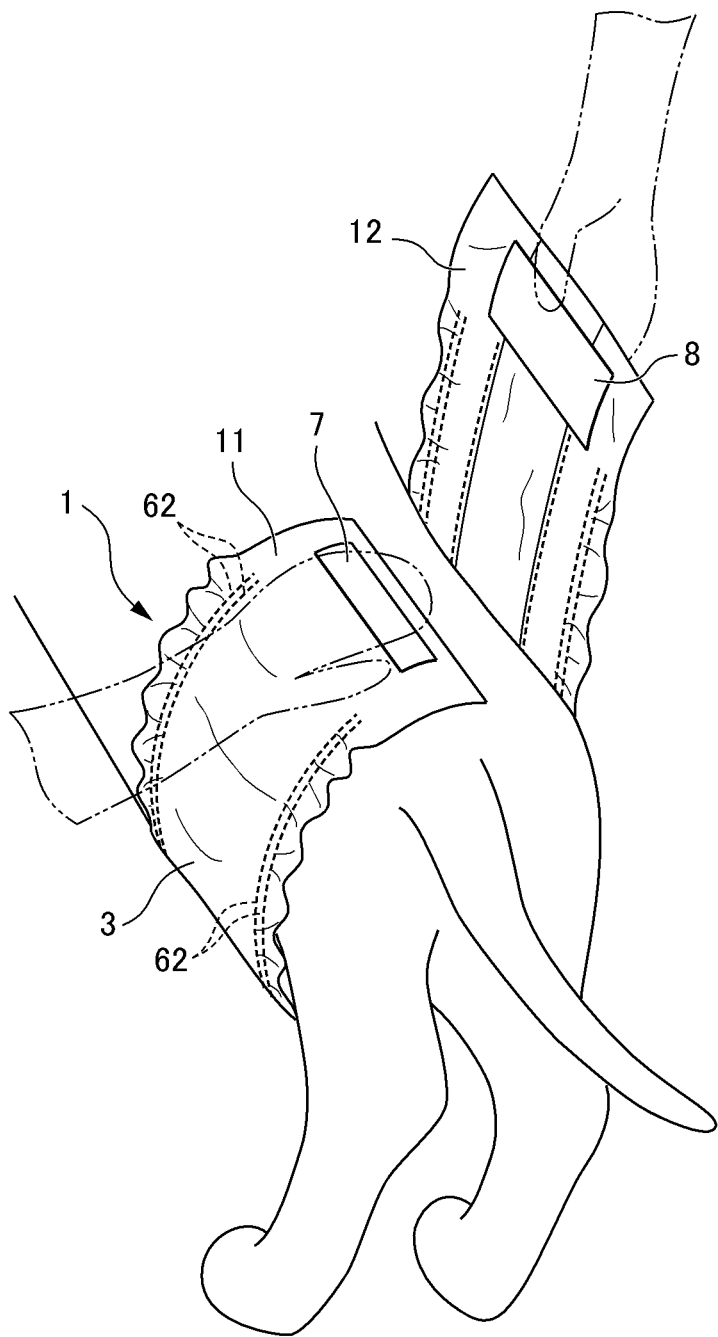
FIG. 7 is a diagram illustrating a process of putting the absorbent article for pet of the first embodiment on a pet, in which the second end portion of the absorbent article for pet wrapped around the waist of the pet is pulled to bring the absorbent article for pet into close contact with the waist of the pet.
Figure 8:
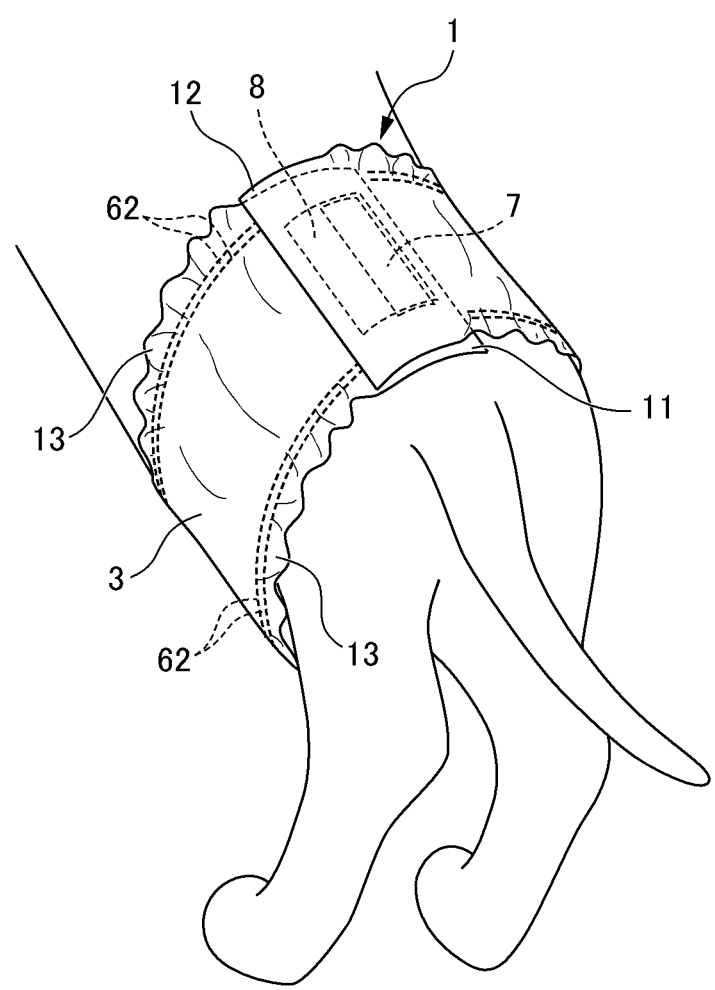
FIG. 8 is a diagram illustrating a process of putting the absorbent article for pet of the first embodiment on a pet, in which the absorbent article for pet is put around the pet's waist.

Next, steps of putting on the absorbent article for pet 1 according to the first embodiment to a pet will be described hereinafter with reference to FIGS. 6 to 8. FIGS. 6 to 8 are diagrams illustrating a process of putting the absorbent article for pet 1 on a pet: FIG. 6 is a diagram illustrating a state in which the first end portion 11 is placed on the pet's back; FIG. 7 is a diagram illustrating a process of putting the absorbent article for pet 1 on a pet, in which the second end portion 12 of the absorbent article for pet 1 wrapped around the waist of the pet is pulled to bring the absorbent article for pet 1 into close contact with the waist of the pet; and FIG. 8 is a diagram illustrating a state in which the absorbent article for pet is put around the pet's waist.

First, as shown in FIG. 6, the first end portion 11 of the absorbent article for pet 1 is placed on the back of the pet and the vicinity of the first end portion 11 is held by one hand of a user. Thereafter, in a state in which the first end portion 11 is held by one hand, the second end portion 12 of the absorbent article for pet 1 is held by the other hand and wrapped around the pet's body to cover the abdomen of the pet.

And then, as shown in FIG. 7, the second end portion 12 is pulled upward to bring a side portion of the absorbent article for pet 1 along the longitudinal direction into close contact with the waist of the pet (a pair of waist gather portions 13 is brought into close contact with the pet's waist). Here, the high stiffness portion is formed in the first end portion 11 of the absorbent article for pet 1. As a result, in a case in which the first elastic member 61 and the second elastic member 62 are extended by pulling the second end portion 12, lift of the first end portion 11 can be suppressed even under a tensile force in the longitudinal direction LD applied to the first end portion 11.

Thereafter, as shown in FIG. 8, the loop member 8 disposed on the inner face of the second end portion 12 is engaged with the hook tape 7 disposed on the outer face of the first end portion. The absorbent article for pet 1 is thus wrapped around the pet's waist.

Here, the bending stiffness of the second end portion 12 of the absorbent article for pet 1 is configured to be smaller than the bending stiffness of the first end portion 11. As a result, the second end portion 12, which is engaged with the first end portion 11 of high stiffness, can flexibly follow the pet's movement wearing the absorbent article for pet 1, and engagement between the first end portion 11 and the second end portion 12 is not easily released even when the pet moves after wearing.

The above-described absorbent article for pet 1 according to the first embodiment provides the following operation and effects.

(1) In the first embodiment, the first elastic member 61 and the second elastic member 62 are disposed in the side portions along the longitudinal direction LD of the absorbent article for pet 1 and, in a natural state, the absorbent article for pet 1 is in a form of being contracted in the longitudinal direction. Given this, in order to bring the absorbent article for pet 1 around the pet's waist in a state of being extended, a user must strongly pull the second end portion 12. The high stiffness portion that is higher in stiffness than the second end portion 12 is therefore formed in the first end portion 11. As a result, in a case in which the second end portion 12 is strongly pulled, the high stiffness portion can suppress lift of the first end portion 11 even under a tensile force in the longitudinal direction LD applied to the first end portion 11. This facilitates engagement of the first end portion 11 with the second end portion 12 upon wrapping the absorbent article for pet 1 around the pet's waist, and the absorbent article for pet 1 can therefore be put easily at the proper position of the pet's body.

(2) Since the bending stiffness of the second end portion 12 is configured to be smaller than the bending stiffness of the first end portion 11, the second end portion 12, which is engaged with the first end portion 11 of high stiffness, can flexibly follow the pet's movement wearing the absorbent article for pet 1. This can prevent the absorbent article for pet 1 from being unfastened even if the pet moves after wearing.

(3) The high stiffness portion is formed by attaching the hook tape 7 having predetermined bending stiffness to the outer face of the first end portion 11. The high stiffness portion can thus be easily obtained by using a member for making the first end portion 11 engaged with the second end portion 12. Since no dedicated member is employed for forming the high stiffness portion, the manufacturing cost of the absorbent article for pet 1 can be reduced.

(4) The hook tape 7 is disposed at a position away from the side edge of the first end portion 11 by a predetermined distance. As a result, in a state in which the first end portion 11 is positioned on the pet's back, if the pet moves and the pet's coat is brought into contact with the outer face of the first end portion 11, the coat is not easily caught by the hook tape 7. Fit of the absorbent article for pet 1 can thus be further improved.

(5) The length W1 of the hook tape 7 is configured to be greater than the length W2 between the first elastic members 61 and the length W3 of the absorbent core 4 in the width direction. As a result, the high stiffness portion can be configured to be elongated in the width direction W of the absorbent article for pet 1 and lift of the first end portion 11 can be suppressed even under a tensile force in the longitudinal direction LD applied to the first end portion 11.

(6) The length W1 of the hook tape 7 is configured to be smaller than the length W4 between the second elastic members 62 disposed respectively on the pair of side portions along the longitudinal direction LD of the absorbent article for pet 1. As a result, the high stiffness portion is not positioned so as to overlap the position where the pair of waist gather portions 13 is formed in the longitudinal direction LD. The high stiffness portion does thus not disturb movement of the pair of waist gather portions 13 during use of the absorbent article for pet 1, thereby improving fit of the absorbent article for pet 1 during use.

Figure 9:
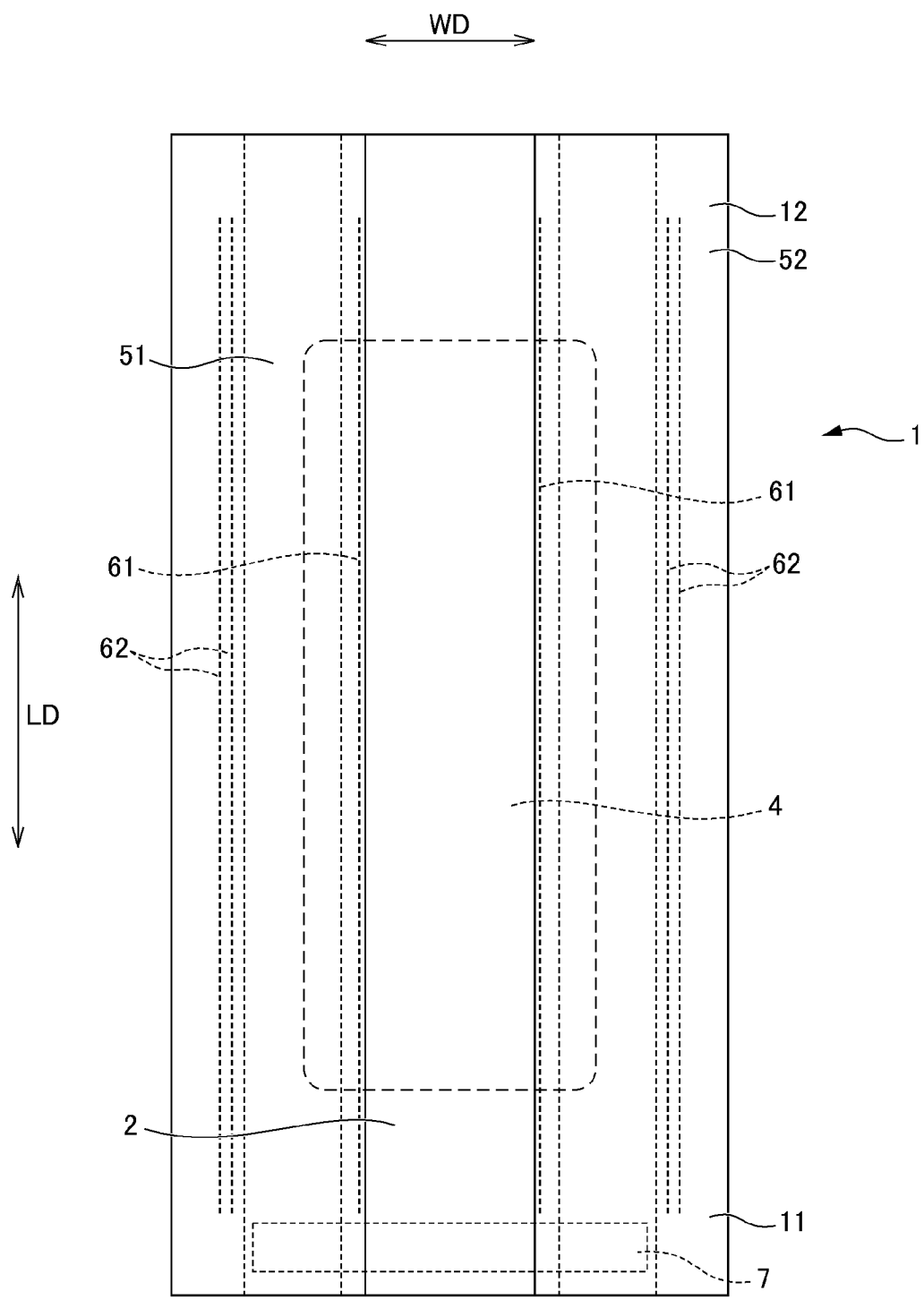
FIG. 9 is a plan view of the absorbent article for pet according to the second embodiment.

The absorbent article for pet 1 according to the second embodiment will be described hereinafter with reference to FIG. 9. FIG. 9 is a plan view of the absorbent article for pet 1 according to the second embodiment.

In the description of the following embodiments, the same constituent features are referred to by the same reference numerals and description thereof is omitted or simplified.

The absorbent article for pet 1 according to the second embodiment is different from the first embodiment in that the loop member is not provided in the second end portion 12.

In the second embodiment, the top sheet 2 and the side sheets 51, 52 are constituted of a nonwoven fabric with which the hook portions 72 of the hook tape 7 can engage. In other words, in the second embodiment, the inner face of the second end portion 12 is constituted of the top sheet 2 and the side sheets 51, 52, and the hook tape 7 engages with the top sheet 2 and the side sheets 51, 52. As the top sheet 2 with which the plurality of hook portions 72 can engage, air through nonwoven fabric and point bonded nonwoven fabric can be exemplified. Among these, an air through nonwoven fabric is preferably used from a viewpoint of obtaining a preferable engaging force with respect to the plurality of hook portions 72. Alternatively, the air through nonwoven fabric can be post-processed by heat embossing. The bonding strength between constituent fibers of the air through nonwoven fabric can thus be increased, to thereby improve resistance of the air through nonwoven fabric to the plurality of hook portions 72 engaging therewith.

As the side sheets 51, 52 with which the plurality of hook portions 72 can engage, point bonded nonwoven fabric, spun bonded nonwoven fabric, spun bonded/melt blown/spun bonded nonwoven fabric and the like can be exemplified.

The absorbent article for pet 1 according to the second embodiment provides the following effects, in addition to the above effects (1) to (6).

(7) The inner face of the second end portion 12 is constituted of the top sheet 2 and the side sheets 51, 52, and the top sheet 2 and the side sheets 51, 52 are constituted of nonwoven fabric with which the plurality of hook portions 72 can engage. As a result, the second end portion 12 with no loop member provided therewith can engage with the first end portion 11, and the manufacturing cost of the absorbent article for pet 1 can thus be reduced. In addition, the second end portion 12 with no loop member provided therewith can engage with the first end portion 11, and the bending stiffness of the second end portion 12 can thus be further reduced. Adherence of the second end portion 12 to the movement of the pet wearing the absorbent article for pet 1 can be further improved.

Figure 10:
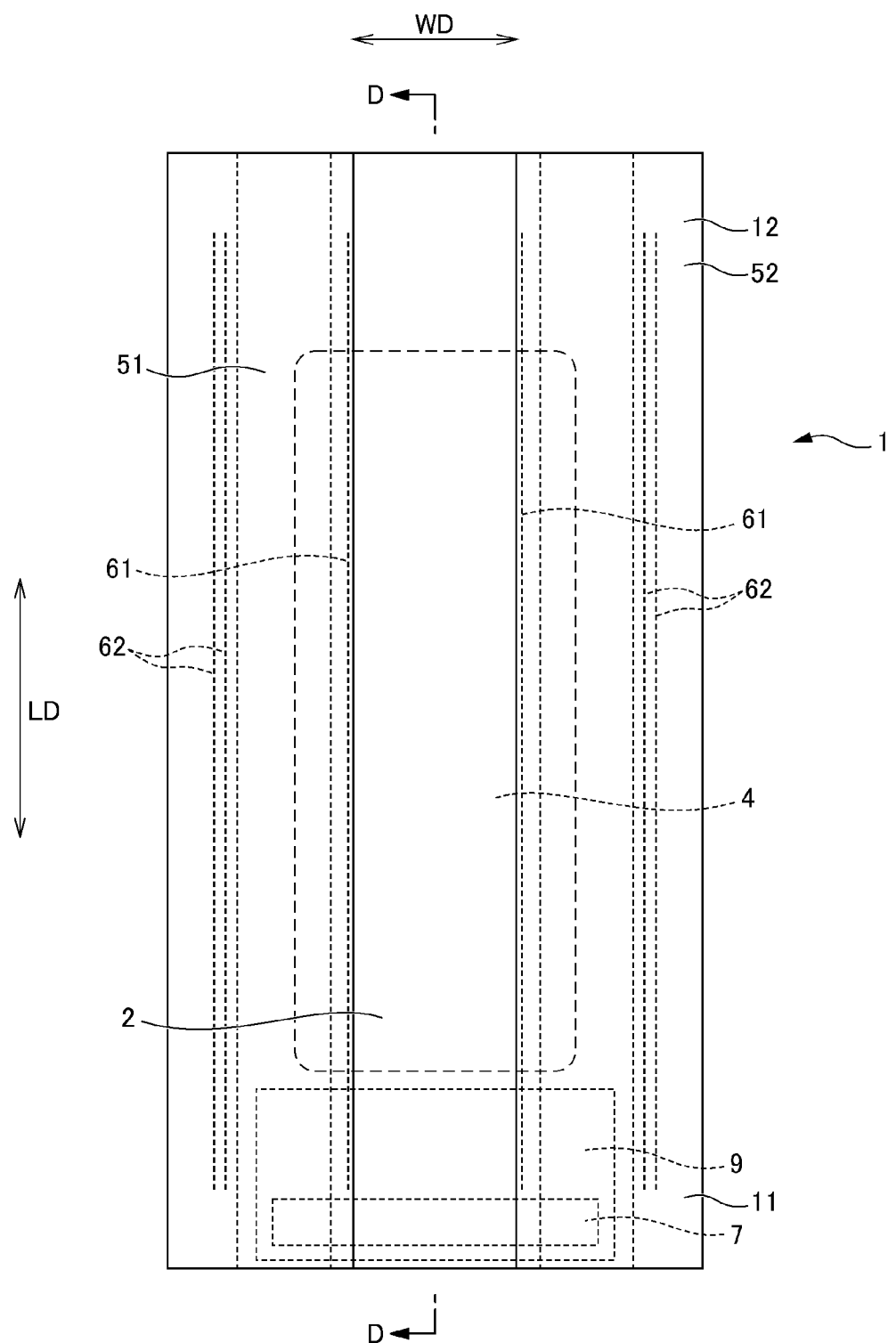
FIG. 10 is a plan view of the absorbent article for pet according to the third embodiment.

The absorbent article for pet 1 according to the third embodiment will be described hereinafter with reference to FIGS. 10 and 11. FIG. 10 is a plan view of the absorbent article for pet 1 according to the third embodiment; and FIG. 11 is a cross-sectional view taken along the line D-D of FIG. 10.

The absorbent article for pet 1 according to the third embodiment is different from the second embodiment mainly in the arrangement of the absorbent core 4.

Figure 11:
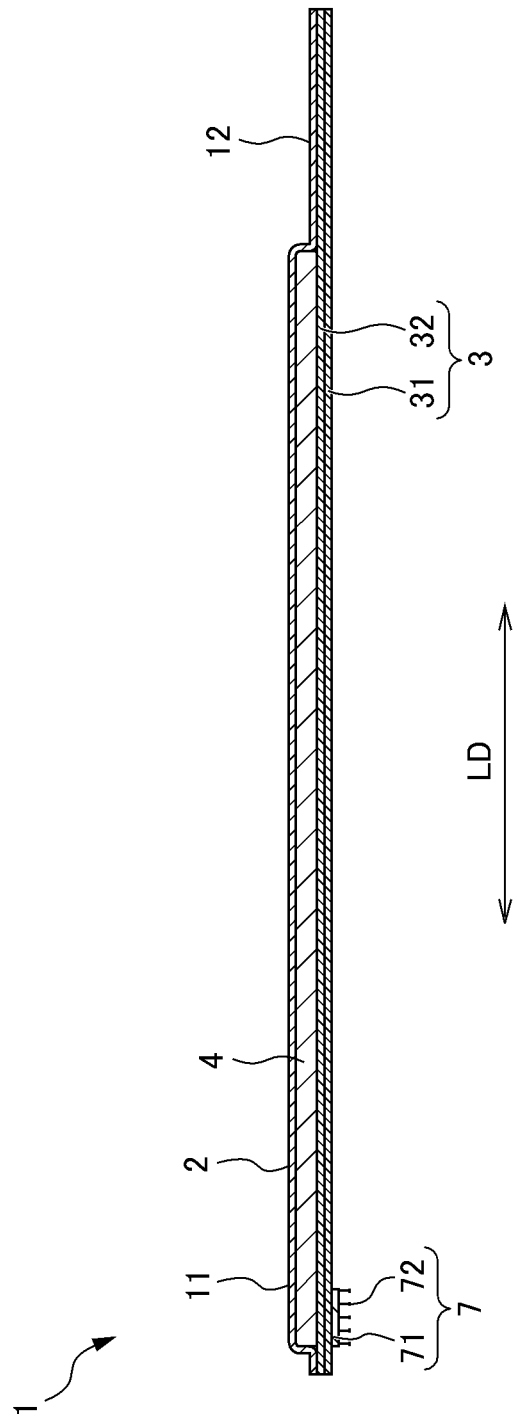
FIG. 11 is a cross-sectional view taken along the line D-D of FIG. 10.

In the third embodiment, the absorbent core 4 is disposed to extend to the first end portion 11, as shown in FIGS. 10 and 11. The absorbent core 4 is not disposed in the second end portion 12. In other words, in the third embodiment, the high stiffness portion is formed by disposing the absorbent core 4 in the first end portion 11.

The absorbent article for pet 1 according to the third embodiment provides the following effects, in addition to the above described effects (1), (2) and (7).

(8) The high stiffness portion is formed by extending the absorbent core 4 to the first end portion 11. The high stiffness portion can thus be formed by using the absorbent core 4 which has been provided. Since no dedicated member is employed for forming the high stiffness portion, the manufacturing cost of the absorbent article for pet 1 can be reduced.

Figure 12:
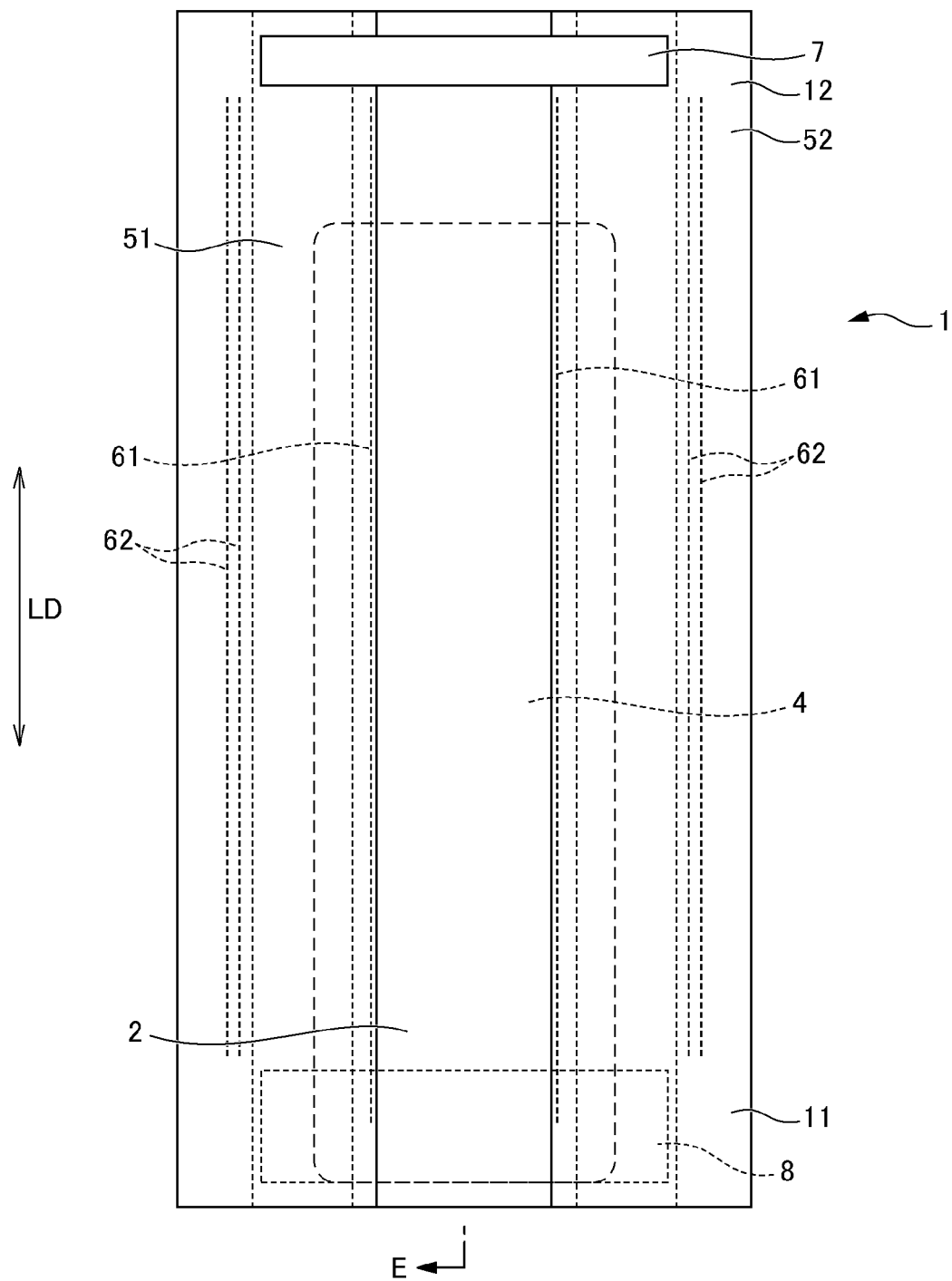
FIG. 12 is a plan view of the absorbent article for pet according to the fourth embodiment.

The absorbent article for pet 1 according to the fourth embodiment will be described hereinafter with reference to FIGS. 12 and 13. FIG. 12 is a plan view of the absorbent article for pet 1 according to the 4 embodiment; and FIG. 13 is a cross-sectional view taken along the line E-E of FIG. 12.

The absorbent article for pet 1 according to the fourth embodiment is different from the third embodiment mainly in the configuration of the first end portion 11 and the second end portion 12.

Figure 13:
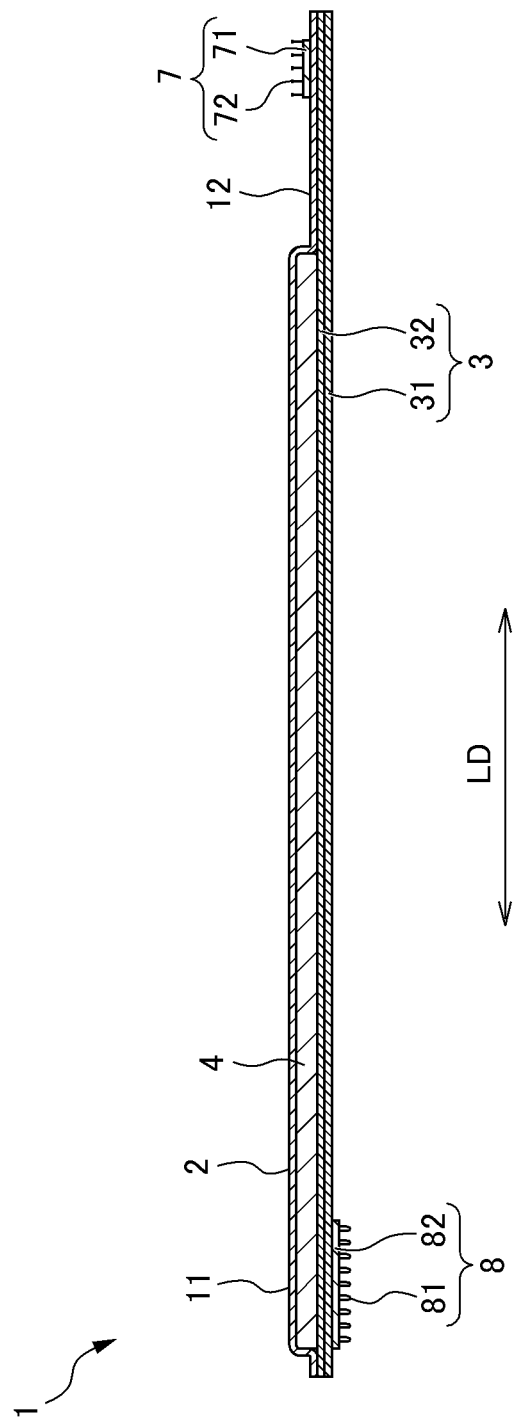
FIG. 13 is a sectional view taken along the line E-E of FIG. 12.

In the fourth embodiment, as shown in FIGS. 12 and 13, the loop member 8 is disposed on the outer face of the first end portion 11 and the hook tape 7 is disposed on the inner face of the second end portion 12.

The absorbent article for pet 1 according to the fourth embodiment provides the above described effects (1) to (2) and (8).

Figure 14:
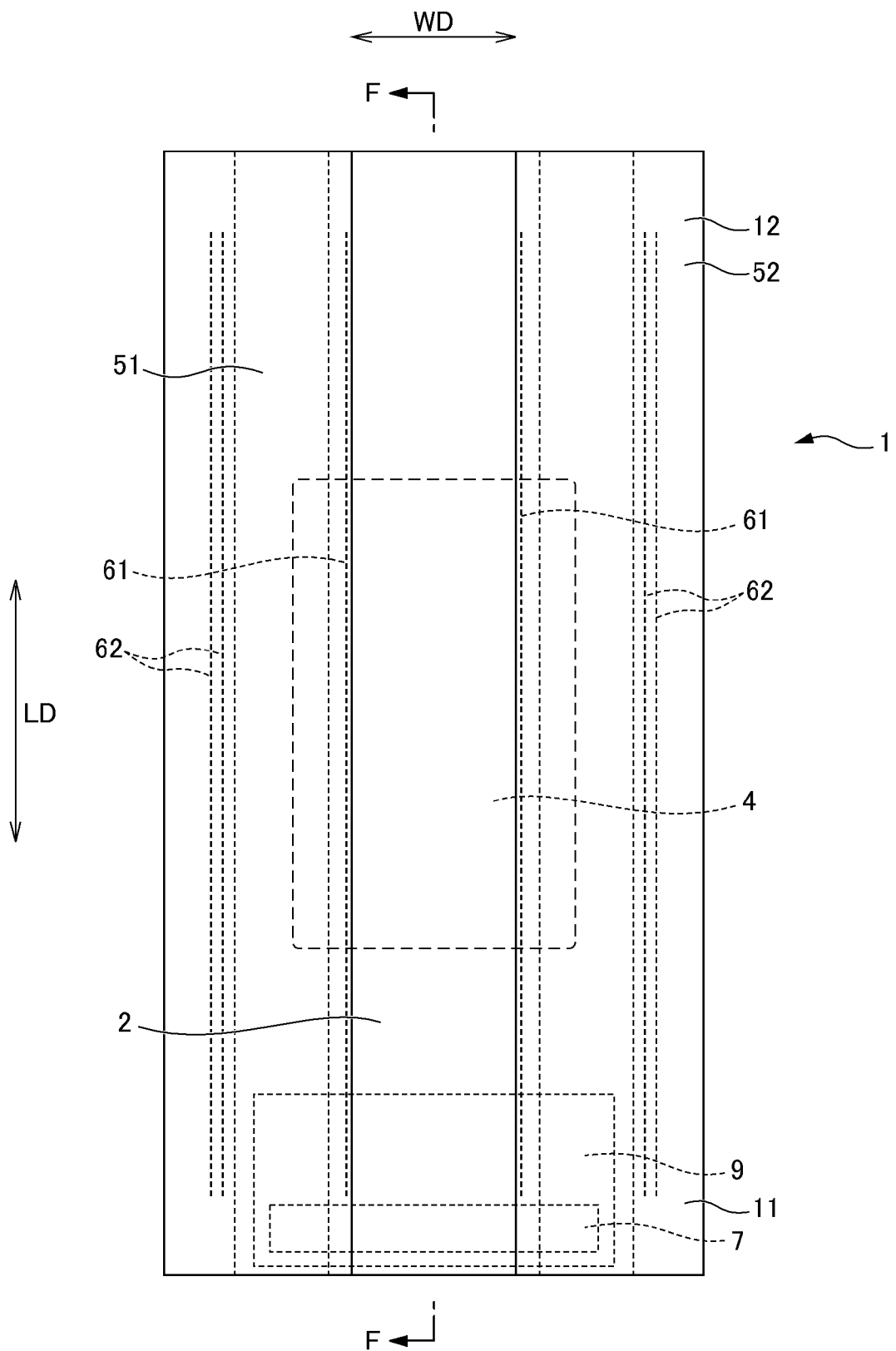
FIG. 14 is a plan view of the absorbent article for pet according to the fifth embodiment.

The absorbent article for pet 1 according to the fifth embodiment will be described hereinafter with reference to FIGS. 14 and 15. FIG. 14 is a plan view of the absorbent article for pet 1 according to the fifth embodiment; and FIG. 15 is a cross-sectional view taken along the line F-F of FIG. 14.

The absorbent article for pet 1 according to the fifth embodiment is different from the second embodiment mainly in the configuration of the first end portion 11.

Figure 15:
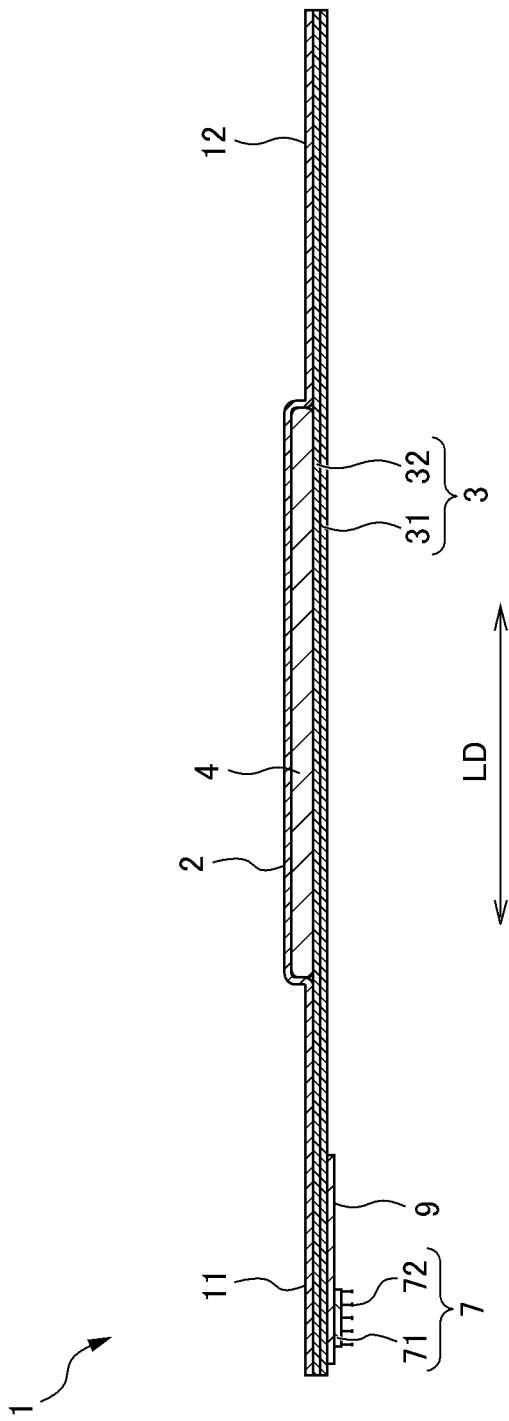
FIG. 15 is a sectional view taken along the line F-F of FIG. 14.

In the fifth embodiment, as shown in FIGS. 14 and 15, a belt-like reinforcing member 9 is disposed on the outer face of the first end portion 11 and the hook tape 7 is disposed on the outer face of the reinforcing member 9. In other words, in the fifth embodiment, the high stiffness portion is configured with the reinforcing member 9. The reinforcing member 9 is obtained by shaping a synthetic resin material such as polypropylene into a sheet having predetermined stiffness.

The absorbent article for pet 1 according to the fifth embodiment provides the above described effects (1) to (2) and (7).

The preferred embodiments of the present invention have been described; however, the present invention is not limited thereto and can be modified accordingly.

For example, in the first to third and fifth embodiments, the hook tape 7 is disposed on the outer face of the first end portion 11, the hook tape 7 being designed to engage with the inner face of the second end portion 12; however, the present invention is not limited thereto. In other words, an adhesive tape in which an adhesive is applied to one face of a base material having predetermined stiffness can be provided on the outer face of the first end portion, the adhesive tape being designed to attach to the inner face of the second end portion. In this case, the inner face of the second end portion can be constituted of a film material that cannot engage with the hook portions.

In addition, in the above described embodiments, the respective inner edges of the first end portion and the second end portion of the front side sheet 51 in the longitudinal direction LD are joined to the top sheet 2, while the inner edges of the rear side sheet 52 is not joined with the top sheet 2; however, the present invention is not limited thereto. In other words, all the inner edges of the first end portion and the second end portion of the front side sheet 51 and the rear side sheet 52 can be joined with the top sheet 2.

Furthermore, in the above described embodiments, the back surface layer 3 is constituted of two layers: the back surface sheet 31 and the waterproof sheet 32; however, the present invention is not limited thereto. In other words, the back surface layer can also be constituted only of the back surface sheet or the waterproof sheet.

The invention claimed is:

1. An absorbent article for pet comprising: a top surface layer that is liquid permeable; a back surface layer that is liquid impermeable; and an absorbent core disposed between the top surface layer and the back surface layer, the absorbent article for pet being configured in a rectangular shape with a first end portion and a second end portion facing each other and a pair of side portions facing each other orthogonal to the first end portion and the second end portion, and configured so that when the absorbent article for pet is worn by a pet by being wrapped around a waist of the pet, the first end portion is positioned on a pet's body side and the second end portion is detachably attached to an outer face of the first end portion, wherein the absorbent article for pet further comprises first elastic members that are disposed along a longitudinal direction of the absorbent article for pet in an extended manner;

a high stiffness portion that is higher in stiffness than the second end portion is formed in the first end portion, a pair of side sheets, which is respectively disposed on a top surface layer side of the pair of side portions, an outer edge of which is joined with the top surface layer or the back surface layer and at least a part of an inner edge of which is a free end; and a pair of pocket portions that is formed between an inner face of the pair of side sheets and an outer face of the top surface layer, wherein the first elastic members are disposed in a vicinity of the inner edge of each of the pair of side sheets, wherein the second end portion includes a substantially linear terminal edge that extends across the entire width of the second end portion in a width direction without having any structure projecting beyond the terminal edge, the high stiffness portion includes a belt-like tape member with a plurality of hook portions and attached to the outer face of the first end portion extending in the width direction of the first end portion; and an inner face of the second end portion is constituted of a nonwoven fabric constituting at least the top surface layer, the nonwoven fabric is configured to be directly engaged with hook portions of the tape member, and wherein the pair of side sheet includes a first side sheet disposed at a front side of the pet's body, and a second side sheet disposed at a rear side of the pet's body, and a configuration by which the first side sheet is joined to the top surface layer is different from a configuration by which the second side sheet is joined to the top surface layer.

2. The absorbent article for pet according to claim 1, further comprising a plurality of second elastic members, wherein ones of the plurality of second elastic member are disposed on one of the pair of side portions and others of the plurality of second elastic members are disposed on another one of the pair of side portions.

3. The absorbent article for pet according to claim 2, wherein the tape member is attached at a position away from an end edge of the first end portion by a predetermined distance, so as to extend in a width direction of the absorbent article for pet.

4. The absorbent article for pet according to claim 1, wherein the tape member is attached at a position away from an end edge of the first end portion by a predetermined distance.

5. The absorbent article for pet according to claim 1, wherein ones of the first elastic members are disposed on one of the pair of side portions and others of the first elastic members are disposed on another one of the pair of side portions.

6. The absorbent article for pet according to claim 5, wherein the tape member is attached at a position away from an end edge of the first end portion by a predetermined distance.

7. The absorbent article for pet according to claim 1, wherein the tape member is attached at a position away from an end edge of the first end portion by a predetermined distance.

8. The absorbent article for pet according to claim 1, wherein an inner edge of the first side sheet is joined with the top surface layer at the first end portion and the second end portion, and an inner edge of the second side sheet is entirely free end along the longitudinal direction of the absorbent article for pet.

\* \* \* \* \*